United States Patent
Hepler

(10) Patent No.: US 11,389,009 B2
(45) Date of Patent: Jul. 19, 2022

(54) BACTERIAL RESISTANT CHAIR

(71) Applicant: John Charles Hepler, Reno, NV (US)

(72) Inventor: John Charles Hepler, Reno, NV (US)

(73) Assignee: VIA, INC, Sparks, NV (US)

(*) Notice: Subject to any disclaimer, the term of this patent is extended or adjusted under 35 U.S.C. 154(b) by 0 days.

(21) Appl. No.: 17/204,751

(22) Filed: Mar. 17, 2021

(65) Prior Publication Data

US 2021/0212476 A1    Jul. 15, 2021

Related U.S. Application Data

(63) Continuation of application No. 15/855,762, filed on Dec. 27, 2017, now Pat. No. 10,986,938.

(60) Provisional application No. 62/439,299, filed on Dec. 27, 2016.

(51) Int. Cl.
| | |
|---|---|
| A47C 31/00 | (2006.01) |
| A61G 5/10 | (2006.01) |
| A61G 15/10 | (2006.01) |
| A61L 2/238 | (2006.01) |
| A47C 3/18 | (2006.01) |
| H01B 1/02 | (2006.01) |
| H01B 7/17 | (2006.01) |
| H01B 17/00 | (2006.01) |
| H02G 15/20 | (2006.01) |

(52) U.S. Cl.
CPC .............. *A47C 31/007* (2013.01); *A61G 5/10* (2013.01); *A61G 15/10* (2013.01); *A61L 2/238* (2013.01); *A47C 3/18* (2013.01); *A61G 2203/70* (2013.01); *H01B 1/02* (2013.01); *H01B 7/17* (2013.01); *H01B 17/005* (2013.01); *H02G 15/20* (2013.01)

(58) Field of Classification Search
CPC .......... A47C 31/007; A47C 3/18; A47C 3/30; A47C 3/04; A47C 7/004; A47C 7/006; A61L 2/238; A61G 5/10; A61G 15/10; A61G 2203/70
USPC .................................................... 297/452.64
See application file for complete search history.

(56) References Cited

U.S. PATENT DOCUMENTS

| | | | | |
|---|---|---|---|---|
| 3,225,431 | A * | 12/1965 | Woodard | A47C 5/04 |
| | | | | 29/419.1 |
| D375,848 | S * | 11/1996 | Grosfillex | D6/367 |
| 6,035,901 | A * | 3/2000 | Stumpf | A47C 5/06 |
| | | | | 139/419 |
| 2011/0016994 | A1 * | 1/2011 | Welsh | A47C 5/12 |
| | | | | 73/866 |

* cited by examiner

*Primary Examiner* — Milton Nelson, Jr.
(74) *Attorney, Agent, or Firm* — Ian Burns; ATIP Law

(57) ABSTRACT

A chair for particular use in clinical or hospital environments has a frame to which a support material is secured. The support material may form a chair back and/or a seat for the chair to provide support to the chair occupant. The support material may be made from a textile of interwoven strands wherein some of the interwoven strands include copper containing particles such as copper iodide or copper oxide within the textile fibers.

8 Claims, 2 Drawing Sheets

BACTERIAL RESISTANT CHAIR

CROSS REFERENCE TO RELATED APPLICATIONS

This application is a continuation of US patent application Ser. No. 15/855762 filed 27 Dec. 2017, now US Pat. No. 10,986,938, which claims priority to U.S. provisional patent application Ser. No. 62/439299, filed 27 Dec. 2016, the contents of which are herein incorporated by reference.

FIELD OF THE INVENTION

The present invention relates to chairs and in particular to chairs used in clinical environments and the like where the surfaces of the chair may be exposed to unsanitary conditions.

BACKGROUND

Clinical areas, hospitals, health centers and the like, require the use of cleaners to reduce the amount of bacteria and other microbes that collect on surfaces. Because of this, fabrics used on furniture, such as chairs, generally need to be sturdy and sufficiently robust to withstand multiple harsh cleaning cycles. Unfortunately, suitable fabrics such as vinyl, hard plastics, etc. tend to be less breathable and therefore less comfortable.

What is required is an improved fabric for use in chairs and similar furniture that can withstand the harsh clinical environment.

SUMMARY OF ONE EMBODIMENT OF THE INVENTION

Advantages of One or More Embodiments of the Present Invention

The various embodiments of the present invention may, but do not necessarily, achieve one or more of the following advantages:

provide a chair with improved cleanable surfaces;
provide a chair for use in clinical environments that can withstand harsh cleaning; and
provide a chair for use in clinical environments that has a breathable fabric.

These and other advantages may be realized by reference to the remaining portions of the specification, claims, and abstract.

Brief Description of One Embodiment of the Present Invention

In one aspect, there is provided a chair. The chair may have a frame that supports a fabric. The fabric provides a support for an occupant of the chair. The fabric may comprise a mesh. The mesh may be comprised of strands, fibers, threads etc. The strands may include one or more strands that include a copper infusion.

In one aspect, there is provided a chair. The chair may have a frame that supports a fabric. The fabric provides a support for an occupant of the chair. The fabric may comprise a mesh. The mesh may be comprised of strands, fibers, threads etc. The strands may include copper containing particles within the strands.

In one aspect, there is provided a chair for particular use in clinical or hospital environments. The chair has a frame to which a support material is secured. The support material may form a chair back and/or a seat for the chair to provide support to the chair occupant. The support material may be made from a textile that includes copper containing particles such as copper iodide or copper oxide within the textile fibers.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description. The invention is capable of other embodiments and of being practiced and carried out in various ways. Also, it is to be understood that the phraseology and terminology employed herein are for the purpose of description and should not be regarded as limiting.

DESCRIPTION OF CERTAIN EMBODIMENTS OF THE PRESENT INVENTION

It is to be understood that other embodiments may be utilized and structural changes may be made without departing from the scope of the present invention.

The present invention, as described herein, includes a chair in which the support fabric is a mesh. Mesh fabrics are rarely used in clinical or hospital environments. The problem with mesh is that it is made of materials that are woven together or intertwined and stretched across the back, and, this material breaks down when cleaned with strong cleaners like bleach.

In the present application, the mesh that is typically used in a mesh chair is replaced with a mesh including copper infused strands. The strands may be, for example, a polymer, nylon or similar type material to which a copper compound such as cuprous oxide, cuprous iodide etc. is added prior to the material being drawn into fibers or strands. In one particular embodiment, the strands are drawn from a polymer in which cuprous iodide particles are dispersed. The cuprous iodide particles may have a size generally between about 0.50 and about 2.0 microns and are dispersed within the polymer to produce a resultant fiber having a percentage weight of approximately 4% cuprous iodide.

The copper infusion has been demonstrated to improve the antibacterial and/or antiviral properties of the material.

Chairs manufactured using copper infused fibers as the mesh material have been tested by the present inventors and shown to be as good or better at reducing the colony count of bacteria as other bacteria reducing fabrics. Without the copper infusion, normal mesh grows bacteria at a rate that is far higher and one that would not be acceptable for hospitals because it can't be cleaned by a high enough concentration of bleach without compromising the mesh to the point it will fail in the chair.

Thus, the mesh chairs as described herein can be used in hospitals and similar clinical environments in a way that they could not before. Many people prefer mesh to vinyl covered foam, hard plastics, etc because it is comfortable, breathable, and slim line.

The present invention comprises a chair. The chair includes a frame over which is applied a mesh fabric that includes a copper infusion as described herein. The frame may be plastic, metal, or any suitable sturdy material. In one embodiment, the mesh has weft yarns with 1200 polyester and warp yarns 2300 denier. The base material of the mesh may be polyester or polyester copolymer. The mesh material may be chosen do have a degree a elasticity and/or resilience to make it suitable and comfortable as a chair support material. The mesh material may be used as the seat support and/or as a backing support to support the occupant in the chair. The mesh may be secured to the frame using any suitable technology known in the art, including sleeves, stitching, fasteners (rivets, screws, pins, staples, etc.) and the like.

Figure 1:
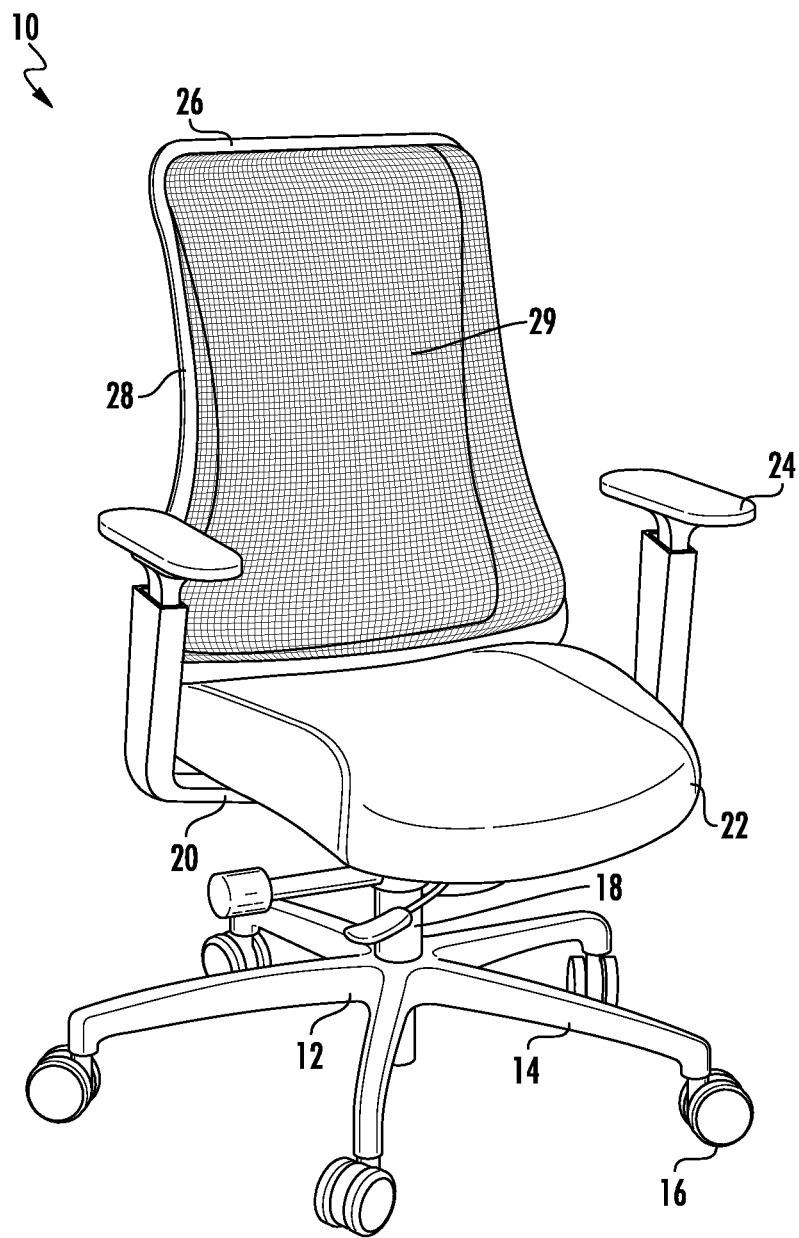
FIG. 1 substantially depicts a swivel chair incorporating a copper fiber mesh portion in accordance with an embodiment of the invention.

A first embodiment of a chair is shown in FIG. 1. In this embodiment, the chair 10 is a swivel chair and includes a base 12 having a plurality of legs 14 extending radially outward from a center. At the end of each leg 14 is a wheel, roller or coaster 16. The middle of the base 12 supports a telescopic stem 18 attached to a chair frame 20. The telescopic stem 18 may utilize a gas strut to raise and lower the height of the chair frame as is known. The chair frame 20 supports a seat 22, arm rests 24, and a chair back 26. The chair back 26 has a chair back frame 28 that forms a perimeter of the chair back 26. Stretched across the chair back frame 28 is a mesh 29 made from the copper infused fabric. The mesh 29 provides the support material for the chair back 26. The mesh 29 may be secured to the chair back frame 28 by any suitable means including clips, staples, stitches, welding, adhesives, etc. In FIG. 1, the seat 22 is an upholstered padded seat, covered with a clinical textile such as a coated vinyl, of which Silvertex is one example. Other forms for the seat 22 will be apparent to the person skilled in the art.

Figure 2:
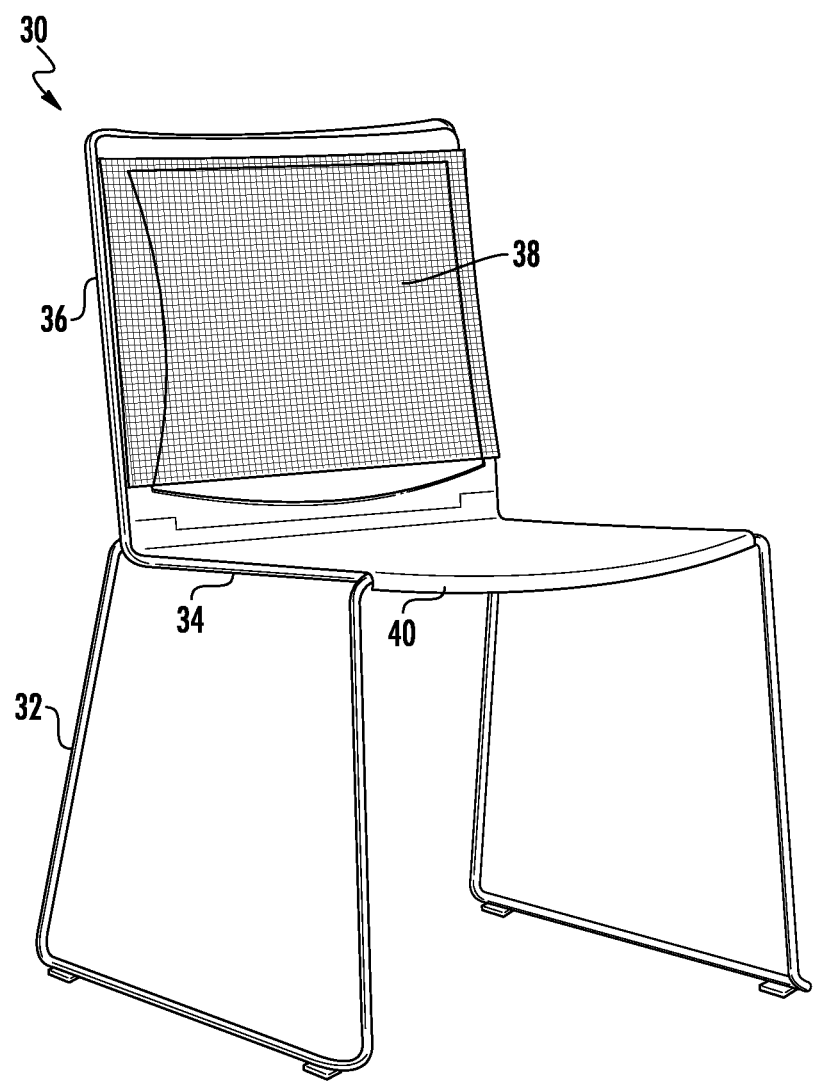
FIG. 2 substantially depicts a second embodiment of a chair incorporating a copper fiber mesh portion.

A second embodiment of a chair is shown in FIG. 2. The chair 30 of this embodiment may include a framework that provides chair legs 32, a chair frame 34 and a chair back frame 36. The copper infused textile fabric may be provided across one or both of the chair frame 34 or chair back frame 36 to provide a support material to support the weight of a chair occupant. In the particular embodiment of FIG. 2, the mesh material is provided as a chair back support material 38 and is secured to the chair back frame 36 by suitable means as described above. The seat 40 is a section of concave plastic shaped for occupant comfort and is provided between left and right portions of the chair frame 34. In alternative embodiments, the seat 40 may be formed of mesh, padded textiles, or other suitable materials.

Although the description above contains many specifications, these should not be construed as limiting the scope of the invention but as merely providing illustrations of some of the embodiments of this invention. Thus, the scope of the invention should be determined by the appended claims and their legal equivalents rather than by the examples given.

What is claimed is:

1. A chair comprising:
    (A) a frame; and
    (B) a support material that is supported by the frame and that provides a support for an occupant of the chair; wherein the support material comprises a mesh having a plurality of interwoven strands, wherein the plurality of interwoven strands comprise one or more interwoven strands that include copper containing particles having a size between 0.50 and about 2.0 microns.

2. The chair of claim 1 wherein the support comprises a chair back.

3. The chair of claim 2 wherein the chair back comprises a chair back frame that provides a perimeter and wherein the mesh is applied across the chair back frame.

4. The chair of claim 1 wherein the copper containing particles comprises copper iodide.

5. The chair of claim 1 wherein the copper containing particles comprises copper oxide.

6. The chair of claim 1 wherein the mesh material is at least partially elastic.

7. The chair of claim 1 wherein the copper containing particles are dispersed within the respective strand to produce a resultant fiber having a percentage weight of approximately 4% copper containing particles.

8. The chair of claim 1 wherein the chair is a swivel chair comprising a base having a plurality of legs extending radially outward from a center.

* * * * *